United States Patent
Strack et al.

(10) Patent No.: US 9,360,424 B2
(45) Date of Patent: Jun. 7, 2016

(54) DEVICE FOR CALIBRATING A SCATTEROMETER

(71) Applicant: ROBERT BOSCH GMBH, Stuttgart (DE)

(72) Inventors: Daniel Strack, Uhingen (DE); Reinhard Hoss, Plochingen (DE); Michael Neuendorf, Plochingen (DE); Gerhard Haaga, Ohmden (DE); Karl Stengel, Deizisau (DE); Andrea Matteucci, Stuttgart (DE)

(73) Assignee: ROBERT BOSCH GMBH, Stuttgart (DE)

( * ) Notice: Subject to any disclaimer, the term of this patent is extended or adjusted under 35 U.S.C. 154(b) by 144 days.

(21) Appl. No.: 14/372,175

(22) PCT Filed: Jan. 14, 2013

(86) PCT No.: PCT/EP2013/050531
§ 371 (c)(1),
(2) Date: Jul. 14, 2014

(87) PCT Pub. No.: WO2013/107702
PCT Pub. Date: Jul. 25, 2013

(65) Prior Publication Data
US 2015/0077749 A1 Mar. 19, 2015

(30) Foreign Application Priority Data

Jan. 19, 2012 (DE) .......................... 10 2012 200 739

(51) Int. Cl.
*G01N 15/06* (2006.01)
*G01N 21/47* (2006.01)

(52) U.S. Cl.
CPC ............ *G01N 21/4785* (2013.01); *G01N 15/06* (2013.01); *G01N 2015/0693* (2013.01); *G01N 2201/06113* (2013.01); *G01N 2201/127* (2013.01)

(58) Field of Classification Search
USPC ................................ 356/335–344
See application file for complete search history.

(56) References Cited

U.S. PATENT DOCUMENTS

| | | | | |
|---|---|---|---|---|
| 3,944,834 A | * | 3/1976 | Chuan | G01N 21/276 250/372 |
| 4,266,220 A | * | 5/1981 | Malinowski | G08B 29/26 250/574 |
| 4,557,599 A | * | 12/1985 | Zimring | G01B 3/02 125/13.01 |
| 4,761,552 A | * | 8/1988 | Rosenthal | G01N 21/4785 250/252.1 |
| 4,980,557 A | * | 12/1990 | Myers | H01J 27/26 250/423 R |
| 6,989,896 B2 | * | 1/2006 | Wen | G01N 21/211 356/243.1 |
| 7,142,299 B2 | * | 11/2006 | Tokhtuev | G01N 21/53 356/338 |
| 7,659,980 B1 | * | 2/2010 | Mitchell | G01N 21/4785 356/338 |
| 7,878,047 B2 | * | 2/2011 | Hemblade | G01N 29/222 73/61.75 |
| 2003/0090666 A1 | * | 5/2003 | Kaufmann | G01N 21/031 356/438 |

FOREIGN PATENT DOCUMENTS

DE 102010002423 9/2011
FR 2858851 2/2005

OTHER PUBLICATIONS

International Search Report for PCT/EP2013/050531, issued on Apr. 15, 2013.

* cited by examiner

*Primary Examiner* — Tri T. Ton
*Assistant Examiner* — Jarreas C Underwood
(74) *Attorney, Agent, or Firm* — Norton Rose Fulbright US LLP

(57) ABSTRACT

A calibration device is described for calibrating a scatterometer, which is designed in particular for measuring a particle concentration in exhaust gases of motor vehicles. The calibration device has at least one scattering body which emits scattered light having a defined intensity and distribution when irradiated with a light beam, the scattering body having an emission surface for the scattered light, to which is assigned at least one light sensor for detecting the scattered light exiting the emission surface. A screening body having at least one screen opening through which the scattered light exits in the direction of the at least one light sensor is assigned to the emission surface of the scattering body.

9 Claims, 6 Drawing Sheets

DEVICE FOR CALIBRATING A SCATTEROMETER

FIELD OF THE INVENTION

The present invention relates to a device for calibrating a scatterometer.

BACKGROUND INFORMATION

The use of scattered light methods for measuring the concentration of particles in gases and other colloids in dispersion media is known from the related art.

German Published Patent Appln. No. 10 2010 002 423 describes such a scatterometer in which a light-intensive light source directs a light beam into a measuring chamber in which the gas or colloid to be measured is located. Assigned to the measuring chamber are two light sensors which detect the light which is scattered on the particles present in the gas. To check the proper function of such a scatterometer or to calibrate it, it is necessary to set a defined condition in the measuring chamber, at which the light beam of the light source emits a scattered light having a defined intensity and distribution.

For that purpose, it is known from German Published Patent Appln. No. 10 2010 002 423 to provide a calibration device, in which a scattering body is used in the measuring chamber, which emits a scattered light having a defined intensity and distribution when irradiated with the light of the light source, the scattered light being detected by the two light sensors. The calibration device should be able to simulate different concentrations of particles in the exhaust gas. It is necessary to simulate exhaust gas values having different particle concentrations using the calibration device. The scattering body is made of a transparent carrier material having defined scattered light properties. In addition, a tinted layer or a gray glass filter for damping the scattered radiation or damping the light output is provided on the exit side of the scattered light in the direction of the light sensors and/or at the entrance side of the light beam into the scattering body.

If the laser beam used as the light source in the above-described calibration device strikes the scattering body, approximately 3% of the light is diffusely scattered in each case on the entrance side and the exit side. This diffusely scattered radiation is visible as a luminous spot (speckle pattern) on the scattering body. The luminous spot is superposed as interference with the scattered radiation produced on the scattering centers in the scattering body, so that the light sensors reach saturation, because the amount of light that falls on them is too great.

SUMMARY

An object of the present invention is to prevent the influence of diffuse scattered radiation on the scattered radiation detected by the light sensors.

The calibration device has the advantage that the effect of the diffuse scattered radiation generated on the scattering body on the at least one light sensor is reduced. This causes the diffuse scattered radiation occurring on the entrance side and the exit side of the scattering body, which generates a luminous spot (speckle pattern), to be largely screened out of the calibrating scattered radiation used for calibrating the light sensors. This also makes it possible to regulate the intensity of the scattered light emitted by the scattering body onto the light sensors in such a way that defined light intensities strike the light sensors in order to calibrate the scatterometer for exhaust gas values having different particle concentrations.

A carrier having a receptacle for the scattering body is provided for the calibration device, the carrier making it possible to position the scattering body in a defined position within a measuring chamber of the scatterometer.

Advantageously, the carrier is designed in the form of a pin which may be inserted into an opening of a housing of the scatterometer, so that the scattering body accommodated in the pin is located within the measuring chamber in a beam path of the light beam.

According to a first specific embodiment, the pin has a section for attaching the screening body and a gap as a receptacle for the scattering body, the pin having, in the area of the beam path of the light beam, a first recess for an entrance opening for the light beam and a second recess for an exit opening for the light beam.

According to a second specific embodiment, the pin is embodied as a hollow cylinder pin having a cylinder wall and having a cavity formed within the cylinder wall, the screening body being formed by the cylinder wall, into which at least one penetration has been introduced as a screen opening. The cavity of the hollow cylinder pin forms the receptacle for the scattering body, an entrance opening for the light beam and an exit opening for the light beam being present in the cylinder wall of the hollow cylinder pin.

The screening body may have a single screen opening which points in the direction of the at least one light sensor; or a screen opening may be provided for each light sensor.

For further attenuation of the diffuse scattered radiation, it is advantageous if the emission surface on the scattering body is additionally provided with a scattering layer. The scattering layer may be carried out by introducing saw cuts into the emission surface or by coatings.

DETAILED DESCRIPTION

Figure 1:
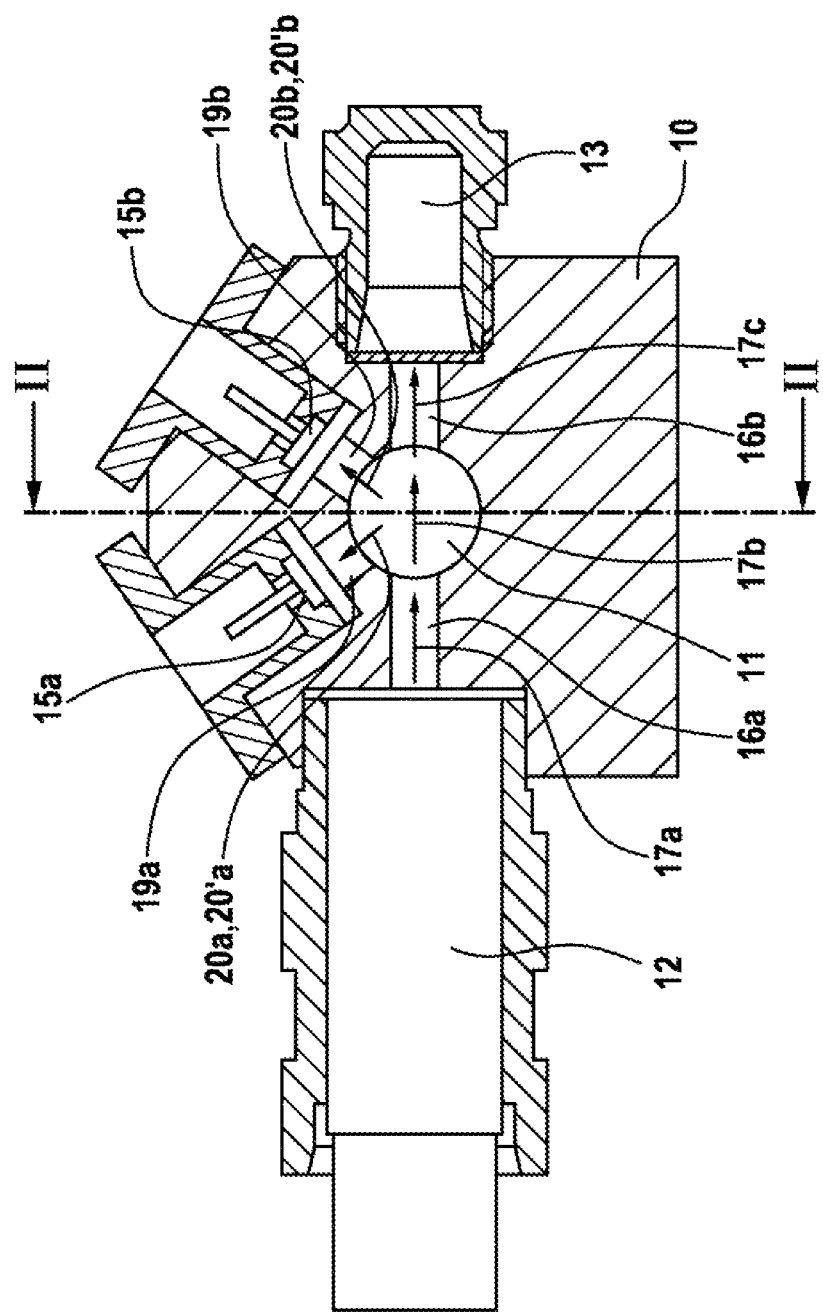
FIG. 1 shows a cross section through a scatterometer.

The scatterometer shown in FIG. 1 is used for measuring a particle concentration in gases or of colloids in a dispersion medium, in particular in exhaust gases of motor vehicles. The scatterometer has a measuring chamber 11 formed in a housing 10, a light source 12, for example, a laser light source, a radiation absorber 13 and two light sensors 15a and 15b. From light source 12, an input-side beam channel 16a leads into the measuring chamber, and an output-side beam channel 16b leads from measuring chamber 11 to radiation absorber 13. Radiation absorber 13 is used for completely absorbing or destroying unscattered or only partially absorbed light of light source 12.

When switched on, light source 12 generates a light beam 17a, preferably a laser light beam which is coupled into measuring chamber 11 at a defined intensity, and extends within measuring chamber 11 as light beam 17b. From measuring chamber 11, beam path 17b of light beam 17a exits as an additional light beam 17c and strikes radiation absorber 13 situated there behind output-side radiation channel 16b.

Two light sensors 15a, 15b are each exposed to measuring chamber 11 in each case via a scattered light channel 19a and 19b. Via scattered light channels 19a, 19b, scattered light 20a, 20b produced in measuring chamber 11 is guided to light sensors 15a, 15b. Light sensors 15a, 15b are preferably situated at different angles with respect to the emission direction of irradiated laser beam 17a, so that the light scattered in measuring chamber 11 is detected from different angles as scattered radiation 20a and 20b. During the measuring operation, the exhaust gas present in measuring chamber 11 causes scattered light 20a, 20b to be generated and detected by light sensors 15a, 15b. The electrical signals generated by light sensors 15a, 15b are supplied to an amplification and evaluation device (not shown), which evaluates the signals and ascertains and outputs the exhaust gas values from the exhaust gas flows guided through measuring chamber 11.

Figure 2:
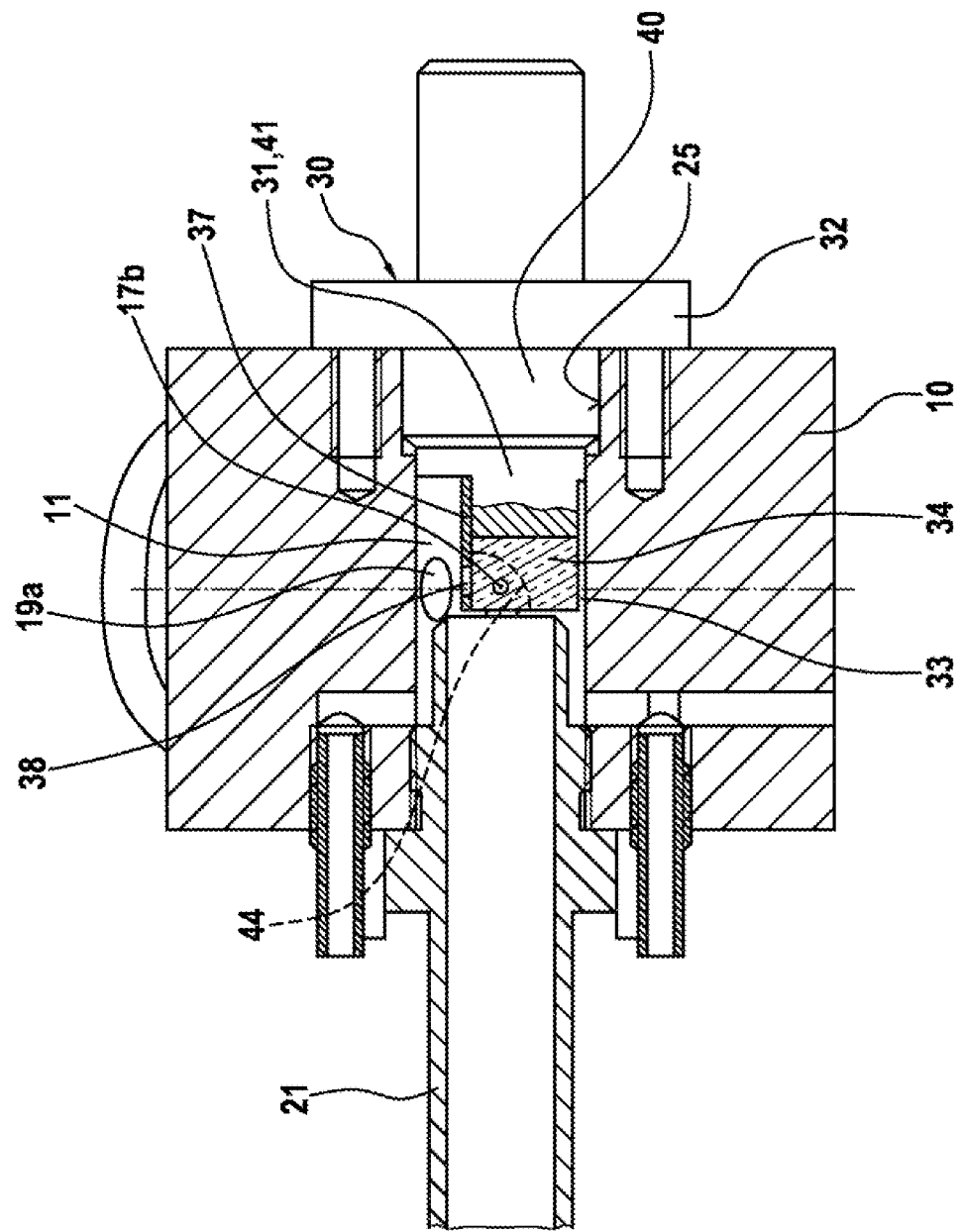
FIG. 2 shows a cross section through the scatterometer in FIG. 1 following the line II-II having a calibration device inserted according to the present invention.

According to FIG. 2, an inlet tube 21 is flange-mounted to housing 10 of the scatterometer, the exhaust gas of the motor vehicle being guided via the inlet pipe into measuring chamber 11. On the diametrically opposed side, an opening 25 is formed on housing 10, to which an outlet tube (not shown) is flange-mounted for the measuring gas in the measuring operation of the scatterometer.

During the calibration operation described below, inlet tube 21 is not connected to the exhaust gas system of the vehicle, or no exhaust gas is introduced from the vehicle into measuring chamber 11. Furthermore, a calibration device 30 is inserted into opening 25 of the scatterometer instead of the outlet tube during the calibration operation. Calibration device 30 is used for calibrating light sensors 15a, 15b of the scatterometer and for monitoring the intensity of light source 12 as well as, if necessary, for detecting a possibly occurring contamination of the optics of light source 12 and/or of light sensors 15a, 15b.

Calibration device 30 includes a carrier 31 having a guide section 40 and a flange 32, carrier 31 being accommodated in opening 25 of the scatterometer with the aid of guide section 40 and being attached to housing 10 with the aid of flange 32. Calibration device 30 is positioned reproducibly in housing 10 of the scatterometer by guide section 40. Furthermore, a receptacle 33 for accommodating a scattering body 34 is formed on carrier 31. Carrier 31 including scattering body 34 protrudes into measuring chamber 11 and is exposed to beam path 17b of light beam 17a within measuring chamber 11. FIG. 2 shows beam path 17b as a beam emerging from the drawing plane. Scattering body 34 is made from a transparent carrier material, such as a glass ceramic, in which a defined number of scattering centers are situated, so that scattering body 34 emits a calibrating scattering radiation 20'a and 20'b in the direction of light sensors 15a, 15b when irradiated by light beam 17a.

Figure 3:
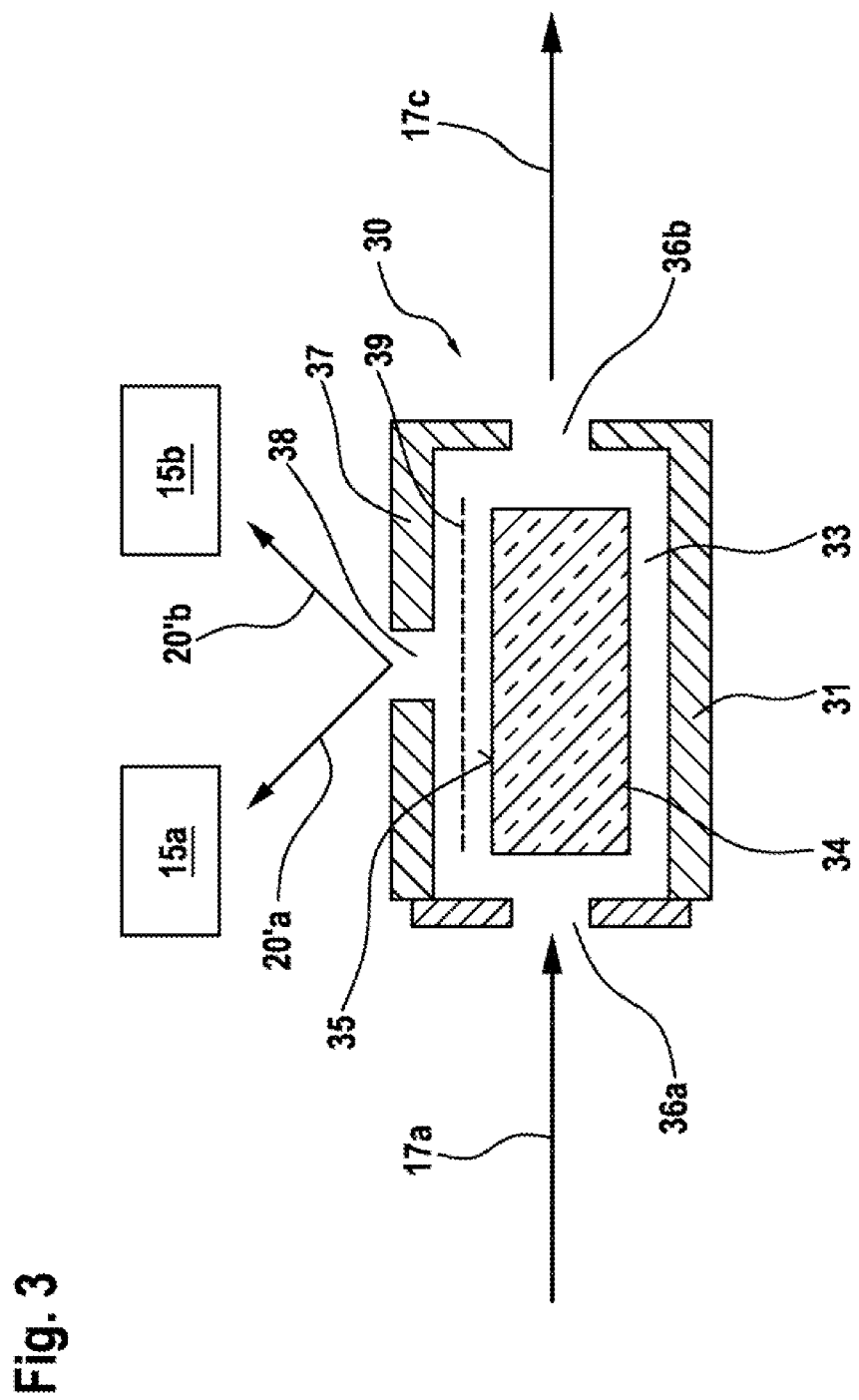
FIG. 3 shows a schematic cross section through a calibration device according to the present invention according to a first specific embodiment.
Figure 4:
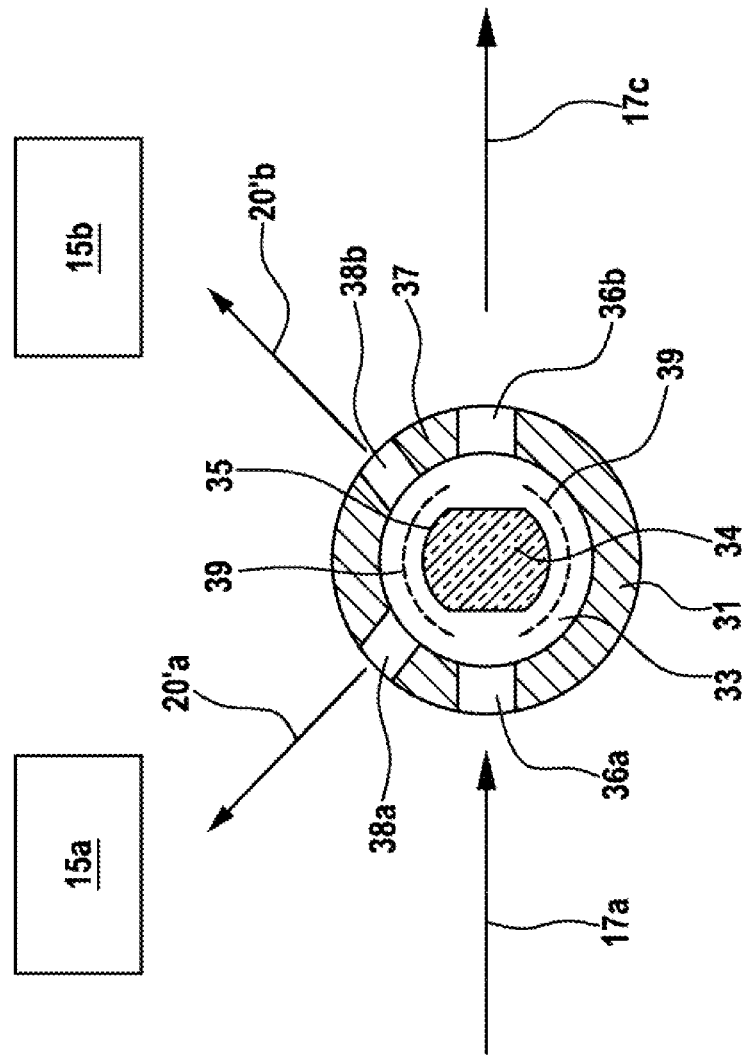
FIG. 4 shows a schematic cross section through a calibration device according to the present invention according to a second specific embodiment.

FIGS. 3 and 4 show schematic specific embodiments of calibration device 30, scattering body 34 being accommodated on carrier 31 in receptacle 33. In carrier 31, an entrance opening 36a is formed for light beam 17a and an exit opening 36b is formed for light beam 17c. Scattering body 34 has an emission surface 35 in the direction of two light sensors 15a, 15b, a screening body 37 having at least one screen opening 38 being assigned to emission surface 35. Screening body 37 is positioned between emission surface 35 and light sensors 15a, 15b. However, screening body 37 may also be situated directly on scattering body 34. In the exemplary embodiment as shown in FIG. 3, a single screen opening 38 is formed. Screen opening 38 is configured and positioned in such a way that scattered radiation 20'a, 20'b of scattering body 34 reaches both light sensors 15a, 15b and strikes light sensors 15a, 15b at a defined intensity, and the interfering diffuse scattered radiation, which is produced when light beam 17a enters into calibration body 34 and when light beam 17c exits calibration body 34, is screened out.

In addition, one or multiple scattering disks 39 may be situated in the emission direction in front of and/or behind screen opening 38, the scattering disks further suppressing the diffuse scattered radiation (speckle pattern), which is produced when light beam 17a enters scattering body 34 and when light beam 17c exits scattering body 34. This effect may be likewise produced by grinding, sawing, or coating of scattering body 34 on emission surface 35 facing light sensors 15a, 15b, in that this causes an additional scattering layer to be produced in a defined expression on emission surface 35 of scattering body 34. Additional scattering disk 39 may be situated within receptacle 33.

Calibration device 30 includes a carrier 31 in the form of a pin 41, on the outer wall of which is formed guide section 40, pin 41 being inserted into opening 25 with the aid of guide section 40. Pin 41 thus protrudes into measuring chamber 11 in such a way that scattering body 34 accommodated on pin 41 is located in beam path 17b of light beam 17a.

Figure 5:
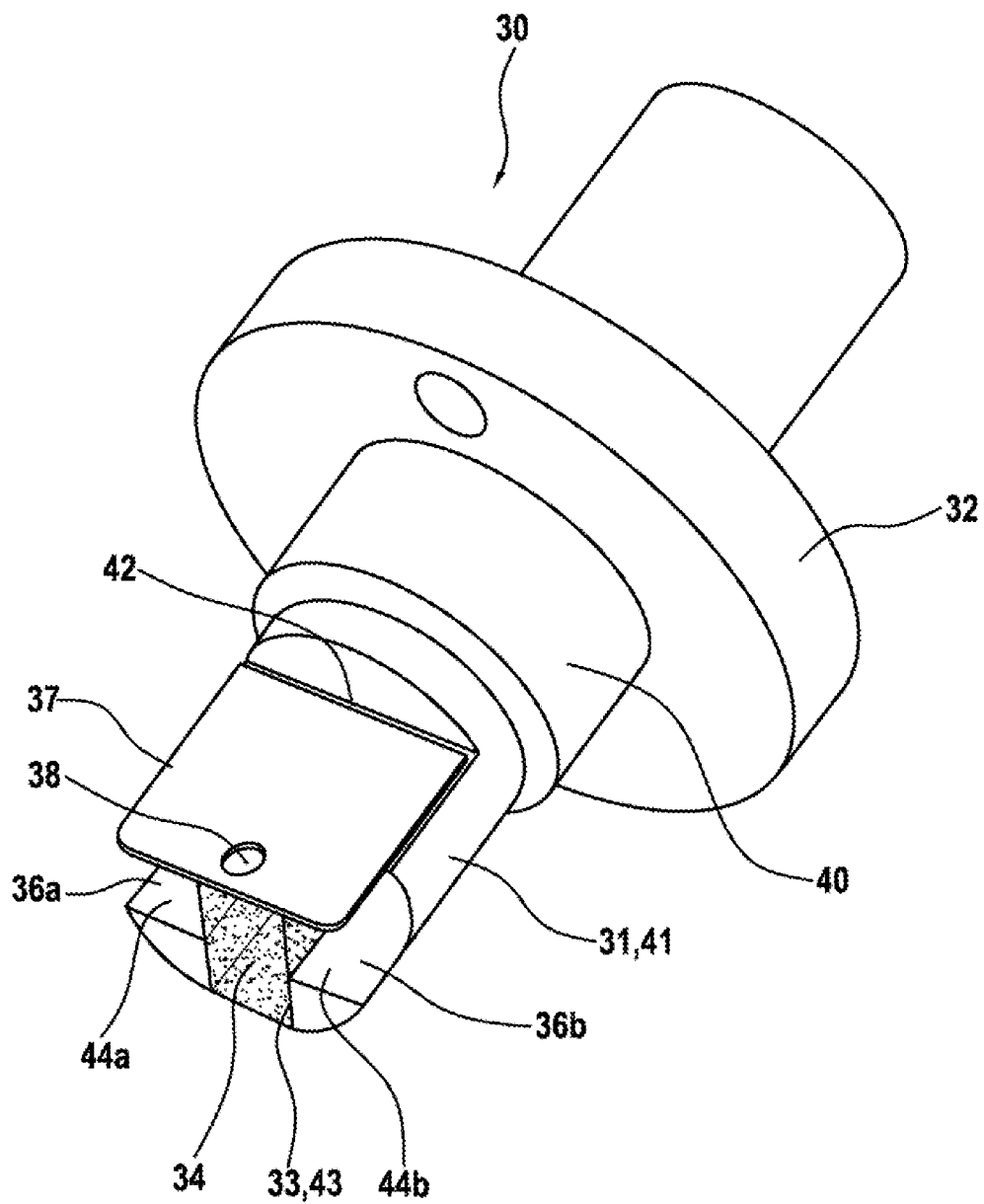
FIG. 5 shows a perspective view of the calibration device according to the present invention according to FIG. 3.

Calibration device 30, which is inserted into measuring chamber 11 in FIG. 2, is shown in greater detail in FIG. 5. Carrier 31 in the form of pin 41 has a section 42 having a flattening for attachment of screening body 37, a gap 43 as a receptacle 33 for scattering body 34 and a first recess 44a for forming entrance opening 36a and a second recess 44b for forming exit opening 36b. Scattering body 34 is inserted into gap 43. Screening body 37 having screen opening 38 is fixed to the flattening in a suitable manner, screen opening 38 being oriented in such a way that the scattered light is guided in the direction of scattered light channels 19a, 19b, and as a result is guided to light sensors 15a, 15b as calibrating scattered radiation 20'a, 20'b. Screening body 37 is attached to carrier 31 in such a way that screen opening 38 maintains a long-term stable and fixed position with respect to scattered light channels 19a, 19b for the calibrations. In the case of the exemplary embodiment shown in FIG. 4, a screen opening 38a and 38b is assigned to each of two light sensors 15a and 15b. Screen opening 38a and 38b is configured in such a way that scattered radiation 20'a, 20'b of scattering body 34 strikes light sensors 15a, 15b at a defined intensity, and the interfering diffuse scattered radiation, which is produced when light beam 17a enters scattering body 34 and when light beam 17c exits scattering body 34, is screened out.

Figure 6:
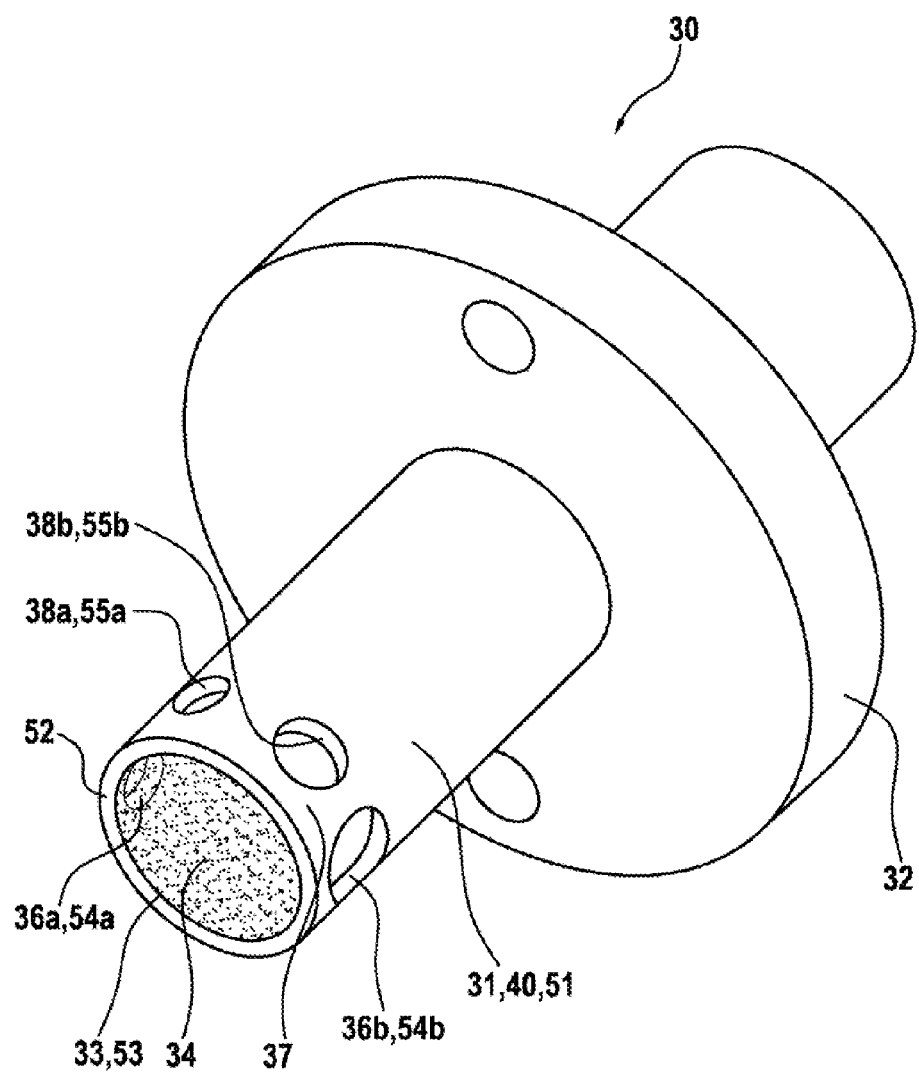
FIG. 6 shows a perspective view of the calibration device according to the present invention in FIG. 4.

A specific embodiment for that purpose is apparent from FIG. 6. There, carrier 31 is designed as a hollow cylinder pin 51 having a cylinder wall 52 and a cavity 53 formed within cylinder wall 52, cylinder wall 52 forming guide section 40. Cavity 53 forms in this case receptacle 33 for scattering body 34. In the emission direction of light beam 17a, a first penetration 54a and a second penetration 54b, which is diametrically opposed to first penetration 54a in the axis of beam path 17b, are introduced into cylinder wall 52 of hollow cylinder pin 51, first penetration 54a forming entrance opening 36a for light beam 17a and second penetration 54b forming exit opening 36b for light beam 17c. A third penetration 55a and a fourth penetration 55b are introduced on the section of cylinder wall 52 facing light sensors 15a and 15b, third penetration 55a forming screen opening 38a for first light sensor 15a and fourth penetration 55b forming screen opening 38b for second light sensor 15b, so that scattered radiation 20'a, 20'b may be guided to light sensors 15a, 15b via screen openings 38a, 38b.

In this exemplary embodiment as well, an additional scattering disk 39 may be situated between hollow cylinder pin 51 and light sensors 15a, 15b, in addition to the screen openings 38a, 38b. It is also possible to accommodate additional scattering disk 39 within cavity 53 of hollow cylinder pin 51, that is, in front of screen openings 38a, 38b. However, it is also possible to provide scattering body 34 inserted into cavity 53 of hollow cylinder pin 51 with a scattering layer having a defined expression, at least on the outside facing screen openings 37a and 37b, by grinding, sawing or coating of emission surface 35.

In another specific embodiment which is not shown, scattering body 34 is not placed into a cavity 53 as shown in FIG. 6. Instead, entrance opening 36a and exit opening 36b form receptacle 33 for a scattering body 34.

What is claimed is:

1. A calibration device for calibrating a scatterometer, comprising:
    at least one scattering body that emits scattered light at a defined intensity and distribution when irradiated by a light beam, wherein the scattering body includes an emission surface for the scattered light;
    at least one light sensor assigned to the emission surface and for detecting the scattered light exiting the emission surface;
    a screening body including at least one screen opening through which the scattered light exits in a direction of the at least one light sensor, the screening body assigned to the emission surface of the scattering body;
    a carrier including a receptacle for the scattering body, wherein on account of the carrier the scattering body is positioned in a defined position within a measuring chamber of the scatterometer, wherein:
        the carrier has a form of a pin that is insertable into an opening of a housing of the scatterometer using a guide section, so that the scattering body accommodated in the pin is located within the measuring chamber in a beam path of the light beam,
        the pin is embodied from a hollow cylinder pin having a cylinder wall and having a cavity formed within the cylinder wall,
        the cylinder wall is insertable into the opening of the housing using the guide section, and
        the screening body is formed from the cylinder wall, into which at least one penetration is introduced for forming the at least one screen opening.

2. The calibration device as recited in claim 1, wherein:
    the pin includes a section for attaching the screening body and a gap as a receptacle for the scattering body, and
    in an area of the beam path of the light beam, the pin includes a first recess for forming an entrance opening for the light beam and a second recess for forming an exit opening for the light beam.

3. The calibration device as recited in claim 1, wherein:
    the cavity of the hollow cylinder pin forms a receptacle for the scattering body, and
    additional penetrations are present in the cylinder wall of the hollow cylinder pin for forming an entrance opening for the light beam and for forming an exit opening for the light beam.

4. The calibration device as recited in claim 3, wherein the entrance opening and the exit opening form the receptacle for the scattering body.

5. The calibration device as recited in claim 1, wherein the screening body has a single screen opening that points in the direction of the at least one light sensor.

6. The calibration device as recited in claim 1, wherein one screen opening each is formed in the screening body for each light sensor.

7. The calibration device as recited in claim 1, further comprising a scattering disk situated in an emission direction one of in front of and behind the screening body.

8. The calibration device as recited in claim 1, wherein the emission surface on the scattering body includes a scattering layer.

9. The calibration device as recited in claim 8, wherein the scattering layer is formed by one of coating, grinding, and introducing saw cuts into the emission surface.

* * * * *